United States Patent [19]

Sagae et al.

[11] Patent Number: 4,857,829
[45] Date of Patent: Aug. 15, 1989

[54] WATER-SOLUBLE OIL PROPERTY DETECTION DEVICE

[75] Inventors: Takashi Sagae, Tokai; Takayuki Kato, Aichi, both of Japan

[73] Assignee: Aichi Steel Works Ltd., Tokai, Japan

[21] Appl. No.: 177,445

[22] Filed: Apr. 4, 1988

[51] Int. Cl.⁴ .................. G01R 27/26; G01N 33/28
[52] U.S. Cl. .................. 324/61 R; 324/65 R; 73/64
[58] Field of Search ........... 324/61 R, 65 R, 57 R; 73/61.1 R, 61 R, 64, 59

[56] References Cited

U.S. PATENT DOCUMENTS

| | | | |
|---|---|---|---|
| 3,768,006 | 10/1973 | Mueller | 324/61 R |
| 3,816,811 | 6/1974 | Cmelik | 324/61 R |
| 4,112,744 | 9/1978 | Tassano | 73/61.1 R |
| 4,240,286 | 12/1980 | Bentz | 73/59 |
| 4,638,305 | 1/1987 | Sutton | 324/65 R X |

Primary Examiner—Reinhard J. Eisenzopf
Assistant Examiner—Jack B. Harvey
Attorney, Agent, or Firm—Burns, Doane, Swecker & Mathis

[57] ABSTRACT

A device for detecting properties of electrically conductive water-soluble oil used in hydraulic pressure-operated devices. The water-soluble oil property detection device is characterized in that it comprises a pair of electrodes placed in a water-soluble oil, a capacitor which is connected in series with the electrodes and which forms a filter circuit with the resistance of the water-soluble oil between the electrodes, a high-frequency power source which has a high-frequency oscillator circuit and a power amplifier and which is connected to both ends of the capacitor and electrodes, and AC-DC converter circuit which detects a high-frequency voltage value occurring at both ends of said capacitor or the resistance between the electrodes and converts the value to a direct current voltage signal, and an indicator part which indicates the output of the converter circuit in correspondence to water-soluble oil property changes.

6 Claims, 7 Drawing Sheets

F I G . 8

| Name of Variable | Viscosity | Moisture | Basicity | PH | Pollution Level | Output Voltage |
|---|---|---|---|---|---|---|
| Viscosity | 1.0000 | | | | | |
| Moisture | -0.8503 ** | 1.0000 | | | | |
| Basicity | 0.4100 ** | -0.1590 | 1.0000 | | | |
| PH | 0.4413 ** | -0.0031 | 0.5511 ** | 1.0000 | | |
| Pollution Level | -0.0545 | 0.2267 | 0.2397 | 0.2753 | 1.0000 | |
| Output Voltage | -0.7531 ** | 0.4450 ** | -0.2598 | -0.7056 ** | -0.0095 | 1.0000 |

WATER-SOLUBLE OIL PROPERTY DETECTION DEVICE

BACKGROUND OF THE INVENTION

The present invention relates to a property detection device that detects changes caused by such factors as oxides, increases in deteriorated products, and changes in water content due to evaporation, in properties of water-soluble oil (such as water-glycol hydraulic oil) used in hydraulic pressure-operated devices.

DESCRIPTION OF THE PRIOR ART

Recently, in response to the rising price of mineral oil and in order to improve safety through fire prevention measures, fire-resistant water-soluble oil has come to replace mineral oil in hydraulic pressure-operated devices that have so-called hydraulic cylinders. For example, water-glycol hydraulic oil, which has ethylene glycol as its principal constituent and has a standard water content of approximately 40%, is an oil with electrical properties approaching those of an electrolytic solution. The smooth operation of hydraulic devices with this water-soluble oil requires that the state of the water-soluble oil be managed on a periodic basis in order to regularly ascertain the water content, quantity of deteriorated products, degree of oxidation and the like, and thereby prevent the occurrence of problems related to seizure, corrosion, or wear of the hydraulic device.

Heretofore, management of hydraulic oil was accomplished by visually observing and comparing the color of new oil and used oil to make a rough determination of the state of deterioration of the used oil. Only hydraulic oil which was deemed to have deteriorated would then be subjected to analytic measurement for water content, with such values as base number and pH measured by the manufacturer as indicators of deteriorated product content. In other words, such values as water content, base number, and pH were measured and analyzed to provide a quantitative basis for judgement because of the difficulty of quantifying judgements based on comparisons of external appearance, which are subject to variation from individual to individual. However, this analytic measurement process required much time and expense, and direct on-site measurements could not be easily performed.

As disclosed in Unexamined Japanese Patent Publication Sho No. 59-60250, a previously known means of detecting the deterioration of oil is the measurement of oil resistance when direct current voltage is applied to the oil, based on the loss of insulating property and the decrease in direct current resistance that accompany the deterioration of oil. However, because water-soluble oil that closely approximates an electrolyte has an extremely low electrical resistance of approximately 1 kilohm-cm, application of direct current voltage causes electrolysis, making measurement impossible. Consequently, it has been difficult to apply this prior art as is to water-soluble oil. Unexamined Japanese Patent Publication Sho No. 58-85314 discloses an engine oil deterioration detection device that detects the deterioration of oil by placing a pair of electrodes in the oil, applying an alternating current voltage, and measuring changes in amplitude and phase to detect increased capacitance or decreased impedance between the electrodes. However, because excessive current flows through electrolytic water-soluble oil, application of this prior art results in a drastic decrease in the output of the alternating voltage power source, making measurement impossible. Consequently, application of this prior art as is to water-soluble oil has also been difficult.

SUMMARY OF THE INVENTION

An object of the present invention is to provide a water-soluble oil property detection device that is compact, lightweight, and simple in structure.

A further object of the present invention is to provide a water-soluble oil property detection device that permits the precise detection and evaluation of decreases in water content and increases in deterioration products of water-soluble oils.

Another object of the present invention is to provide a property detection device that permits the prompt measurement of the properties of water-soluble oil at the site where said water-soluble oil is being used.

An additional object of the present invention is to provide a property detection device that permits the steady detection of changes in electrical resistance that accompany changes in the properties of water-soluble oil, without causing electrolysis or the like in said water-soluble oil.

Yet another object of the present invention is to provide a property detection device that permits the prominent detection of minute changes in resistance that accompany changes in the properties of water-soluble oil.

In order to accomplish the aforementioned objects, the present invention provides a water-soluble oil property detection device comprising a pair of electrodes placed in a water-soluble oil, a capacitor which is connected in series with said electrodes and which forms a filter circuit with the resistance of said water-soluble oil between said electrodes, a high-frequency power source which comprises a high-frequency oscillator circuit and a power amplifier and which is connected to both ends of said capacitor and electrodes, an AC-DC converter circuit which detects high-frequency voltage occurring at both ends of said capacitor and converts said voltage to a direct current voltage signal, and a display portion which displays the output of said converter circuit in correspondence to water-soluble oil property changes.

The aforementioned structure provides an accurate indication of water-soluble oil property changes and the causes thereof because as the water content of the water-soluble oil decreases, the resistance between the electrodes increases, thereby causing the high-frequency voltage to fall below the reference value of the display means, whereas when the deterioration product content of the water-soluble oil increases, the resistance between the electrodes decreases, thereby causing the high-frequency voltage to rise above the reference value of the display means.

The water-soluble oil property detection device of the present invention allows the application of a large, high-frequency current to the water-soluble oil that is to be measured. Consequently, the stable detection of changes in electrical resistance that accompany property changes in said water-soluble oil is possible even for electrolytic, low-resistance water-soluble oils, without incurring a decrease in the output of the high-frequency power source or causing electrolysis in the water-soluble oil.

Further, the low resistance of water-soluble oil is measured by effectively utilizing the drastic high-frequency attenuation characteristic of a filter circuit formed by the resistance r created by the water-soluble oil disposed between a pair of electrodes and a capacitor C1 that is serially connected to said electrodes. Consequently, minute changes in resistance that accompany water-soluble oil property changes are readily detected.

Other objects, characteristics, and advantages of the present invention are further clarified by the following description.

BRIEF DESCRIPTION OF THE DRAWINGS

FIG. 8 is a chart showing a comparison of output voltage with viscosity, water content, basicity, pH, and pollution level, in the form of a correlation matrix.

DETAILED DESCRIPTION OF THE PREFERRED EMBODIMENT

An embodiment of the water-soluble oil property detection device of the present invention is described below with reference to the accompanying drawings.

Figure 1:
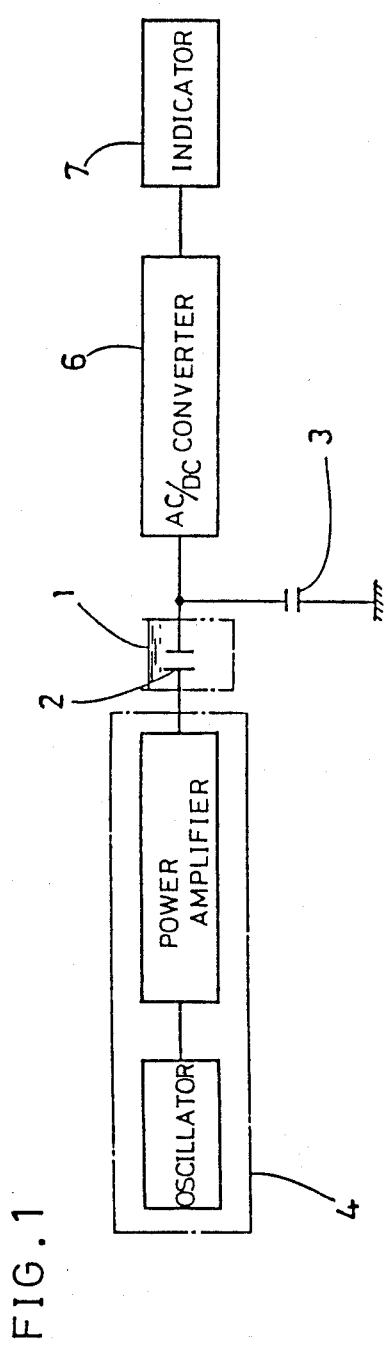
FIG. 1 is a block diagram showing an embodiment of the property detection device of the present invention.

As FIG. 1 shows, a pair of electrodes 2 is placed inside a container filled with a water-soluble oil 1, and a capacitor 3 is connected in series to electrodes 2. An oscillator connected via a power amplifier forms a high-frequency power source 4 that passes high-power, high-frequency current to the series circuit formed by electrodes 2 and capacitor 3. The high-frequency voltage occurring at both ends of capacitor 3 is passed through AC-DC converter 6 to indicator 7, which forms a display means.

Figure 2:
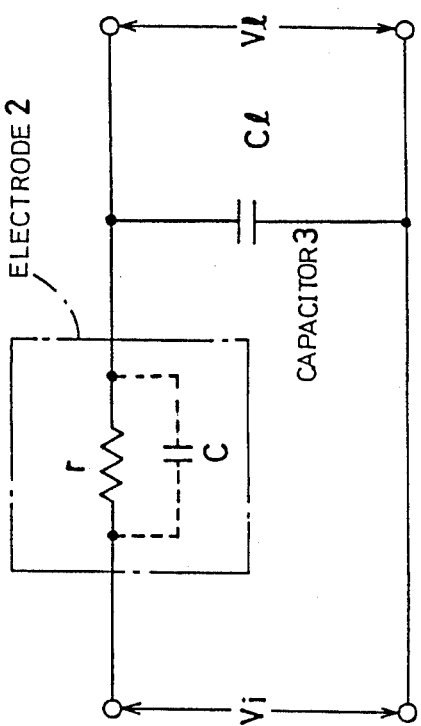
FIG. 2 is a circuit diagram showing an equivalent circuit of the device illustrated in FIG. 1.

FIG. 2 shows an equivalent circuit for the device illustrated in FIG. 1. The capacitance C and resistance r created by water-soluble oil 1, which forms a conductive dielectric between the pair of electrodes 2, exist in parallel. However, because resistance r is small, there is virtually no dependence relative to capacitance C at high frequencies.

Figure 3:
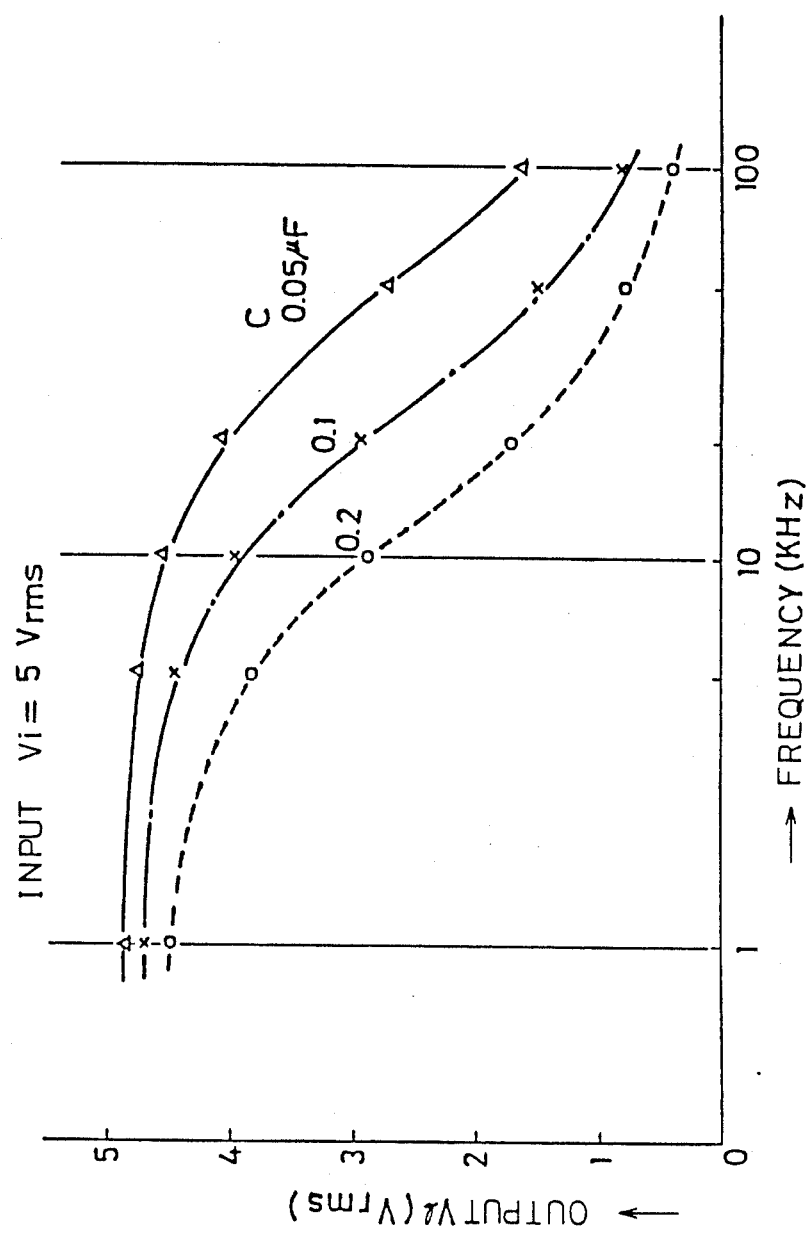
FIG. 3 is a characteristic diagram showing frequency characteristics of the aforementioned equivalent circuit.

Given a diameter of 20 mm and an electrode gap of 1 mm for electrodes 2, the electrical resistance between electrodes 2 at normal temperatures is approximately 100 ohms when new water-glycol hydraulic oil is placed in the container of FIG. 1. The equivalent circuit comprising electrodes 2 and capacitor 3 appears as shown in FIG. 2. As mentioned above, the resistance of water-soluble oil 1 is extremely small, so that the impedance of the capacitance C of water-soluble oil 1 is extremely large for high frequencies. The effect of capacitance C on the equivalent circuit is therefore negligible. The equivalent circuit thus forms a filter circuit from resistance r of water-soluble oil 1 and capacitance C1 of capacitor 3. FIG. 3 illustrates changes in the high-frequency voltage V1 that is output from both ends of capacitor 3 in the aforementioned equivalent circuit when the values of capacitor 3 are 0.05 $\mu$F, 0.1 $\mu$F, and 0.2 $\mu$F, a constant input voltage Vi is applied from high-frequency power source 4, and the frequency of voltage Vi is varied. As FIG. 3 clearly indicates, the attenuation characteristic of a low-pass filter is obtained from the equivalent circuit of FIG. 2. Given a capacitance C1 for capacitor 3, the impedance Z1 of capacitor 3 is:

$$Zl = \frac{1}{\omega c}$$

and the relationship of input Vi to output V1 is therefore:

$$Vl = Vi \cdot \frac{Zl}{r + Zl} \tag{1}$$

For example, when r=Z1, V1 is then 0.5 Vi, an attenuation by $\frac{1}{2}$ of input Vi. When C1=0.05 $\mu$F to 0.2 $\mu$F, output V1 as expressed by Equation (1) changes markedly between approximately 10 kHz and 50 kHz, as FIG. 3 indicates, i.e., the attenuation characteristic of the filter circuit changes markedly according to the size of capacitance C1 of capacitor 3. A drastic attenuation characteristic is particularly evident for frequencies at which r=Z1.

Figure 4:
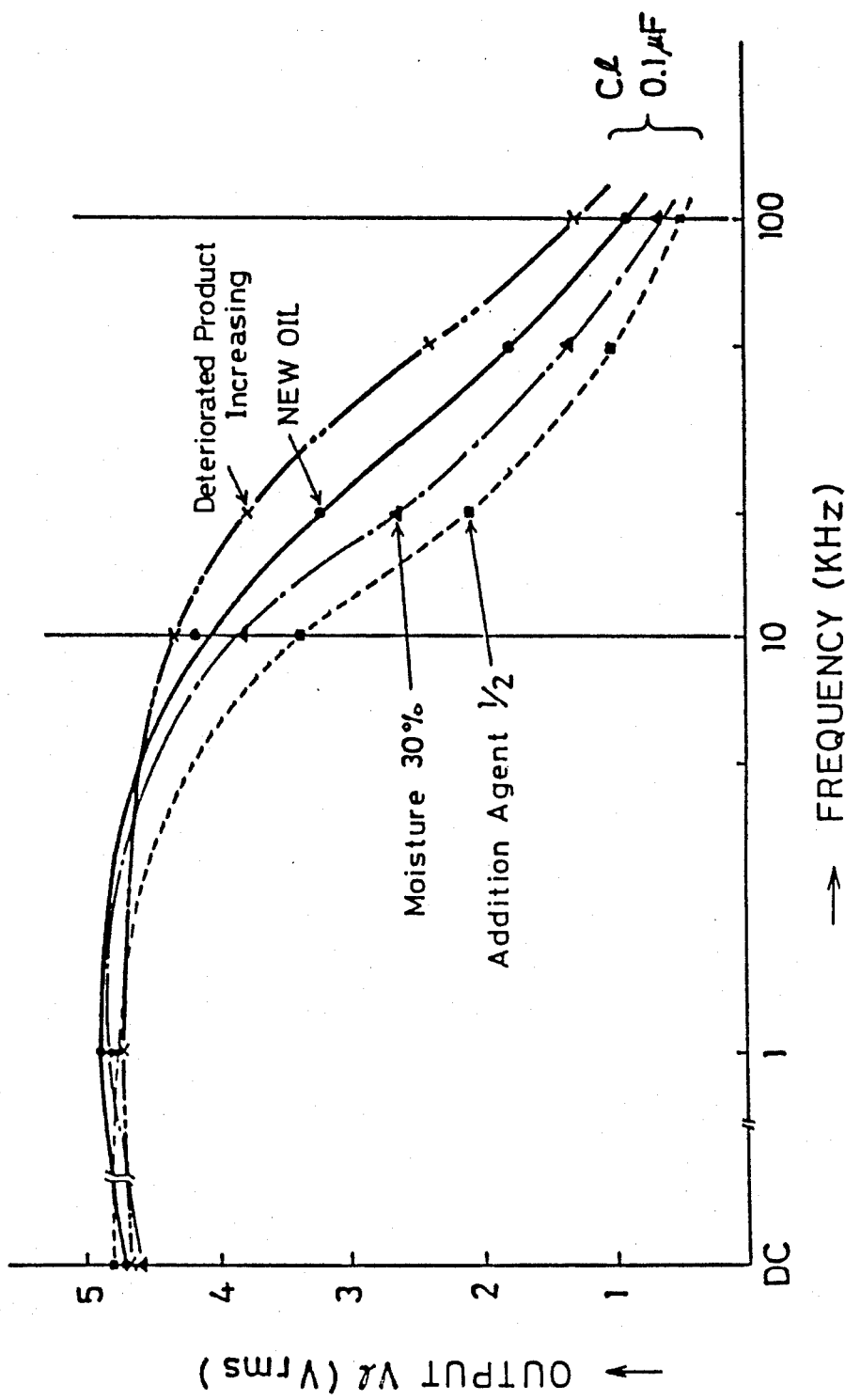
FIG. 4 is a characteristic diagram showing frequency characteristics related to properties of water-soluble oil.

Based on the characteristics shown in FIG. 3 and calculations made using Equation (1), it is predicted that if capacitance C1 of capacitor 3 as shown in FIG. 2 is set at a constant value and resistance r of water-soluble oil varies, attenuation characteristics similar to those of FIG. 3 will result. FIG. 4 illustrates the frequency characteristics obtained when the capacitance of capacitor 3 in FIG. 2 is set at C1=0.1 $\mu$F and the properties of water-soluble oil 1 are changed, thereby changing resistance r. The frequency characteristics shown in FIG. 4 are as follows: black dots indicate new water-glycol hydraulic oil, crosses indicate oil with increased deteriorated products, triangles indicate oil with water content reduced from 40% to 30%, and squares indicate oil with an addition agent (alkaline additive for preventing oxidation of oil) reduced by $\frac{1}{2}$.

As is clear from the figures, the frequency attenuation characteristic of water-soluble oil varies markedly with the properties of the oil. For example, the value of output V1 varies markedly between frequencies of 10 kHz and 50 kHz according to the properties of the oil. In other words, according to Equation (1), output V1 changes in proportion to changes in resistance r of the water-soluble oil, and resistance r changes markedly with the properties of the water-soluble oil. The present invention thus permits the measurement of the properties of electrolytic water-soluble oil by measuring the electrical resistance hat corresponds to said properties without causing electrolysis in said oil. More specifically, changes in the properties of water-soluble oil 1 can be detected by forming a filter circuit from a capacitor 3 and the water-soluble oil 1 that is interposed between a pair of electrodes 2, setting high-frequency power source 4 to a frequency in the frequency band in which the high-frequency attenuation characteristic of said filter circuit exhibits a drastic change, and applying a high-frequency voltage to said filter circuit. The resulting high-frequency output voltage V1, which is output from both ends of capacitor 3 and which changes in correspondence to the properties of said water-soluble oil, is converted to a direct current voltage signal by an AC-DC converter. This signal is then compared to reference values obtained by measuring new oil.

The aforementioned method thus permits measurement of the electrical resistance of oil by passing a sufficient high-frequency current through the oil that is the object of measurement without causing electrolysis in said oil. This method is therefore effective as a means of measuring the low resistance of conductive solutions.

Figure 5:
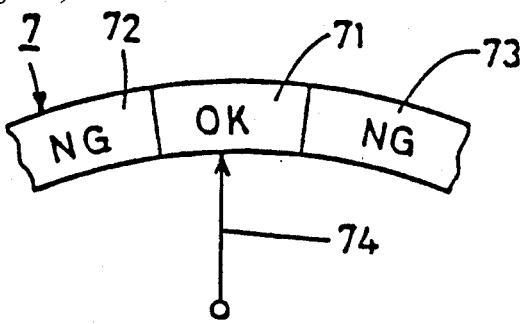
FIG. 5 is a front view illustrating the display method of the present embodiment.

In the present embodiment, indicator 7 consists of a direct current voltmeter. As FIG. 5 shows, the scale of indicator 7 comprises an acceptance zone 71 determined by preset values of a certain range, and rejection zones 72 and 73 at either end of acceptance zone 71. Needle 74 of indicator 7 is placed so that it is capable of pointing out any one of zones 71 to 73 on the scale.

Figure 6:
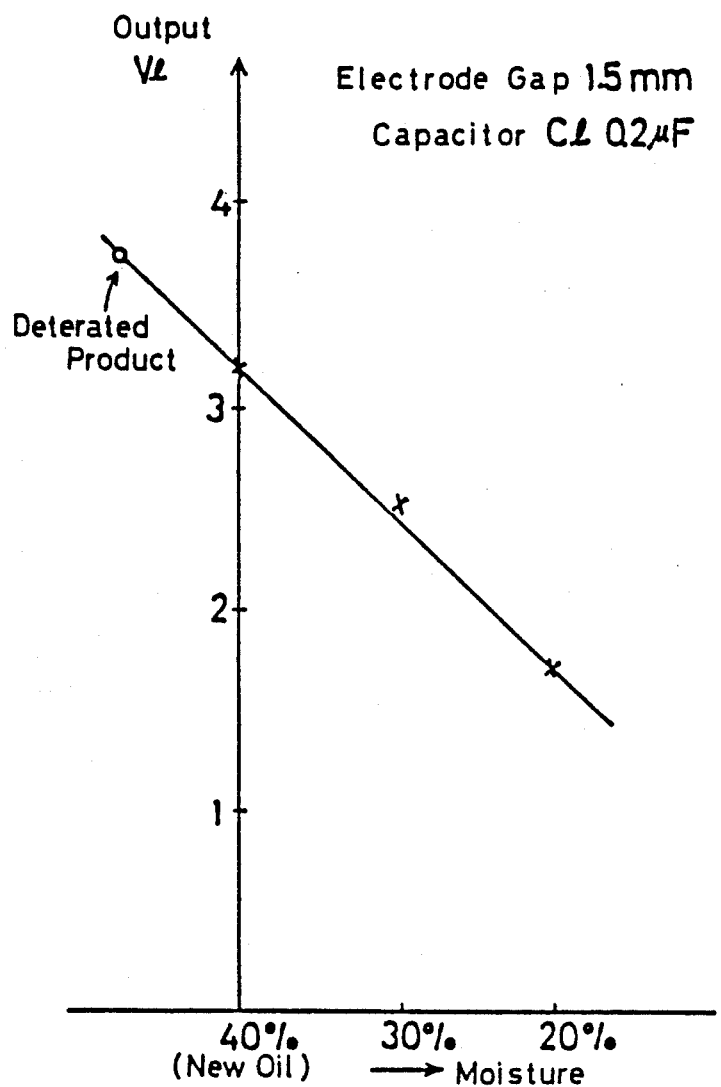
FIG. 6 is a characteristic diagram showing an example of measurement.

FIG. 6 shows an example of actual measurement by the water-soluble oil property detection device of the present invention having the configuration shown in FIG. 1 and the characteristics shown in FIGS. 3 and 4. The adaptability of the present invention was verified by comparing used oil with new oil, using the following samples of water-glycol type water-soluble oil: new oil having 40% water content, oil in which water content was reduced to approximately 20% and 30% respectively, and oil contaminated with deteriorated products. This adaptability test was conducted with an input voltage Vi of 5 V, a frequency of 10 kHz for high-frequency power source 4, a gap of 1.5 mm for electrodes 2, and a capacitance of 0.2 μF for capacitor 3. Test results, as shown in FIG. 6, were as follows. (1) Output voltage V1 decreased in proportion to the decrease in water content of the oil. This result is considered due to increases in resistance over that of new oil. (2) Output voltage V1 was greater for used oil or deteriorated product-contaminated samples than for new oil. This result is considered due to increased conductivity and decreased resistance associated with an increase in oxidation products in the oil due to use or to deteriorated product contamination. The aforementioned test results confirmed that water-soluble oil property changes caused by such factors as reduced water content, reduced additives, or increased deteriorated products, can be measured with a high degree of accuracy by selecting measurement conditions such as the frequency of high-frequency power source 4, the capacitance of capacitor 3, and the gap between electrodes 2.

Figure 7:
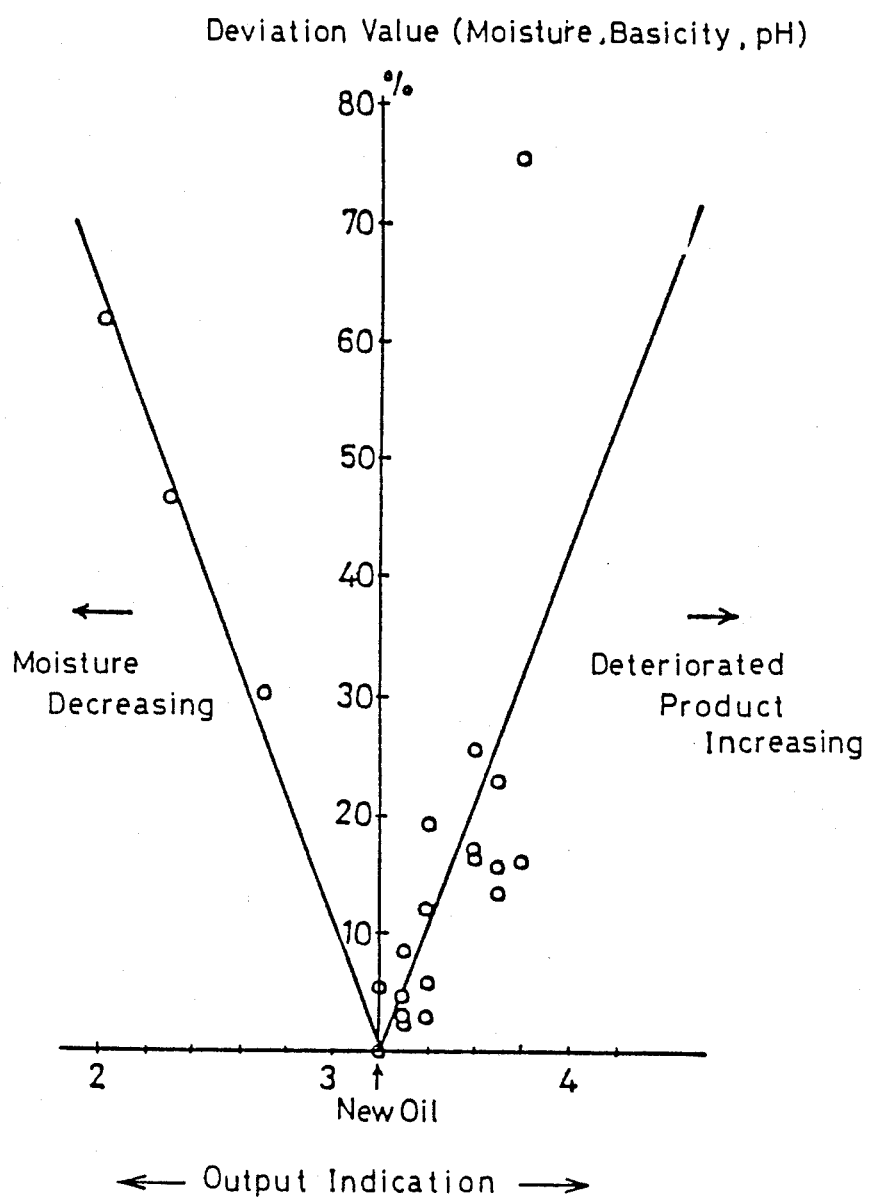
FIG. 7 is a characteristic diagram showing an example of measurement against the deviation values of oil sample analysis values.

FIG. 7 shows one example of the correspondence between the results of measurement by the property detection device of the present invention and a comprehensive evaluation of the analysis (using water content, base number, and pH value as indicators) applied to the quantitative measurement of property changes in water-glycol hydraulic oil.

In FIG. 7, the voltage measured by said property detection device is correlated with the absolute sum of the allowable deviation values (%) for the water content, base number and pH value respectively of several oil samples. These deviation values were calculated by the following equation from the analysis value and reference value of each indicator. For water-glycol hydraulic oil, for example, the common reference values used were 40%+3% for water content, 10±1 for pH, and 150±20 (HC1 ml/100 ml) for base number.

deviation value =

$$\left| \frac{\text{reference value} - \text{analysis value}}{\text{reference value}} \times 100(\%) \right|$$

For example, the deviation value for 38% water content is:

$$\frac{40 - 38}{40} \times 100 = 2\%$$

and the deviation value for a base number of 130 is:

$$\frac{150 - 130}{150} \times 100 = 13.3\%$$

The results shown in FIG. 7 confirmed the following four points regarding water-glycol hydraulic oil. (1) When the deviation value exceeds 20%, the analysis value of either water content, basicity, or pH deviates from the reference value range. (2) When the deviation value is between 10% and 20%, at least one of the analysis values is close to the reference value range. (3) When the deviation value is less than 10%, all of the analysis values are within the reference value range. (4) There is a good correlation between the deviation value and the measured output voltage value, and a range of 3.0 to 3.4 V for this measured value may be considered normal.

FURTHER EMBODIMENT

FIG. 8 shows a comparison of output voltage with viscosity, water content, basicity, pH, and pollution level, in the form of a correlation matrix. The following multiple regression expression was determined from this correlation matrix:

output voltage = +0.0178 × viscosity + 0.0061 × base number − 0.6116 × pH + 9.4727 (2)

It is evident from the above multiple regression expression that output voltage decreases when pH increases, and that output voltage increases when basicity and viscosity values increase.

Figure 9:
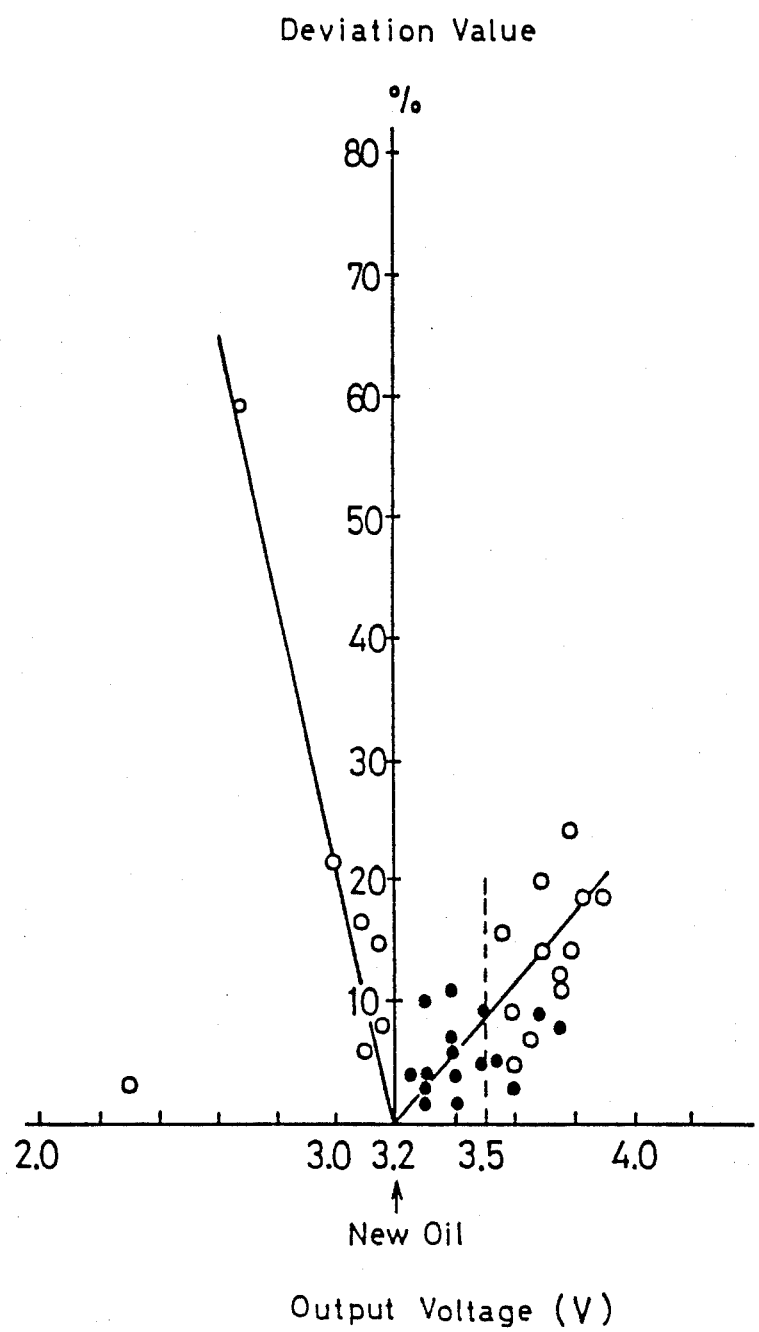
FIG. 9 is a characteristic diagram showing the relationship between output voltage and deviation values of new oil and deteriorated oil.

Optimum voltage values may be selected according to FIG. 9, which shows test results indicating the relationship between output voltage and deviation values for new oil and deteriorated oil. In FIG. 9, black dots indicate that all deviation values for viscosity, pH, and basicity were within the norm, and white dots indicate that at least one of the deviation values was outside the norm. FIG. 9 confirms that water-soluble oil is normal when the voltage value is in the range of 3.2 to 3.5 V, and that either viscosity, basicity, or pH is abnormal when the voltage is less than 3.2 V or greater than 3.5 V. The normality or abnormality of water-soluble oil can thus be determined from the indicator device.

Although the invention has been described in its preferred form with a certain degree of particularity, it is understood that the present disclosure of the preferred form has been changed in the details of construction and the combination and arrangement of parts may be resorted to without departing from the spirit and the scope of the invention as hereinafter claimed.

What is claimed is:

1. A device for detecting a lubricating and rust preventing property of water-soluble oil used in hydraulic pressure-operated devices, said device comprising:
   a pair of electrodes placed in the water-soluble oil;
   a capacitor connected in series between one end of said pair of electrodes and ground and forming a filter circuit with the resistance of said water-soluble oil between said pair of electrodes;
   a high-frequency power source including a high-frequency oscillator circuit and a power amplifier and which is connected across the series combination of said capacitor and pair of electrodes;
   an AC-DC converter circuit for detecting a high-frequency voltage value occurring across said capacitor and for converting said value to a direct current voltage signal; and
   an indicator for indicating the output of said converter circuit in correspondence to changes in said property of said water-soluble oil,
   said high-frequency power source generating a high-frequency voltage of a frequency at which the voltage occurring across said capacitor is in a range of about one-fifth to four-fifths of the voltage generated by said high-frequency power source.

2. A device for detecting a lubricating and rust-preventing property of water-soluble oil as claimed in claim 1, said high-frequency power source generating a high-frequency voltage of a frequency at which the voltage occurring across said capacitor is about half of the voltage generated by said high-frequency power source.

3. A device for detecting a lubricating and rust-preventing property of water-soluble oil as claimed in claim 1, wherein each of the electrodes making up said pair has a diameter of about 20 mm and is separated from the other electrode by an electrode gap having a width in the range from about 1 mm to about 1.5 mm, wherein said capacitor has a capacitance in the range from about 0.05 $\mu$F to about 0.2 $\mu$F, wherein said high-frequency power source generates a high-frequency voltage of a frequency in the range from about 10 kHz to about 100 kHz, and preferably from about 20 kHz to about 50 kHz, and wherein the voltage occurring across said capacitor is indicated by the indicator via the AC-DC converter circuit.

4. A device for detecting a lubricating and rust-preventing property of water-soluble oil as claimed in claim 1, wherein said indicator comprises a direct current voltmeter, the scale of said voltmeter including an acceptance zone determined by preset values of a certain range, and rejection zones at either end of the acceptance zone.

5. A device for detecting a lubricating and rust-preventing property of water-soluble oil used in hydraulic pressure-operated devices, said device comprising:
   a pair of electrodes placed in a water-soluble oil;
   a capacitor which forms a filter circuit with the resistance of said water-soluble oil between said electrodes, said pair of electrodes being connected in series between one end of said capacitor and ground;
   a high-frequency power source including a high-frequency oscillator circuit and a power amplifier and which is connected across the series combination of said capacitor and electrodes;
   an AC-DC converter circuit which detects a high-frequency voltage value occurring across said electrodes and converts said voltage value to a direct current voltage signal; and
   an indicator part which indicates the output of said converter circuit in correspondence to the water-soluble oil property changes, said high-frequency power source generating a high-frequency voltage of a frequency wherein the voltage occurring across said pair of electrodes is in a range of about one-fifth to about four-fifths of the voltage generated by said high-frequency power source.

6. A water-soluble oil property detection device as claimed in claim 5, said high-frequency power source generating a high-frequency voltage of a frequency wherein the voltage occurring across said pair of electrodes is about half of the voltage generated by said high-frequency power source.

* * * * *